United States Patent [19]

Kisida et al.

[11] Patent Number: 4,663,339
[45] Date of Patent: May 5, 1987

[54] ACARICIDAL AND INSECTICIDAL SUBSTITUTED 1-PHENYLALKYLBENZIMIDAZOLES

[75] Inventors: Hirosi Kisida, Tokyo; Haruyasu Yamamoto, Takarazuka; Toshihiko Yano, Ikoma, all of Japan

[73] Assignee: Sumitomo Chemical Company, Limited, Osaka, Japan

[21] Appl. No.: 811,397

[22] Filed: Dec. 20, 1985

[30] Foreign Application Priority Data

Dec. 24, 1984 [JP] Japan ................ 59-278578

[51] Int. Cl.$^4$ ................ A01N 43/52; C07D 235/06; C07D 235/08; C07D 235/10
[52] U.S. Cl. ................ 514/394; 548/325; 548/327; 548/330; 548/332
[58] Field of Search ........... 548/325, 327, 332, 330; 514/394

[56] References Cited

U.S. PATENT DOCUMENTS 4,118,487  10/1978  Regel et al. ................ 548/335

*Primary Examiner*—Richard A. Schwartz
*Assistant Examiner*—Kurt G. Briscoe
*Attorney, Agent, or Firm*—Birch, Stewart, Kolasch & Birch

[57] ABSTRACT

A compound of the formula:

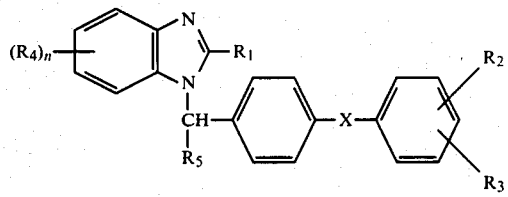

wherein $R_1$ is a hydrogen atom, a lower alkyl group or a halo(lower)alkyl group, $R_2$ and $R_3$ are, the same or different, each a hydrogen atom, a halogen atom, a nitro group, a cyano group or an optionally substituted lower alkyl, lower alkenyl, lower alkynyl, cyclo(lower)alkyl, lower alkoxy, lower alkenyloxy, lower alkynyloxy, cyclo(lower)alkoxy, lower alkylthio, lower alkenylthio, lower alkynylthio, cyclo(lower)alkylthio, di(lower)alkylamino, lower alkylsulfonyl or lower alkylsulfinyl group, or $R_2$ and $R_3$ are combined together to form an optionally substituted 5- or 6-membered, saturated or unsaturated ring optionally having not more than two oxygen or sulfur atoms in the ring, $R_4$ is a halogen atom or a lower alkyl group, $R_5$ is a hydrogen atom or a lower alkyl group, X is an oxygen atom, a sulfur atom, a methylene group, a sulfonyl group, a sulfinyl group or an imino group and n is an integer of 1 to 4, which is useful as an insecticide and/or an acaricide.

12 Claims, No Drawings

ACARICIDAL AND INSECTICIDAL SUBSTITUTED 1-PHENYLALKYLBENZIMIDAZOLES

The present invention relates to benzimidazole derivatives. More particularly, the present invention relates to benzimidazole derivatives (hereinafter referred to as "benzimidazole(s) (I)") of the formula:

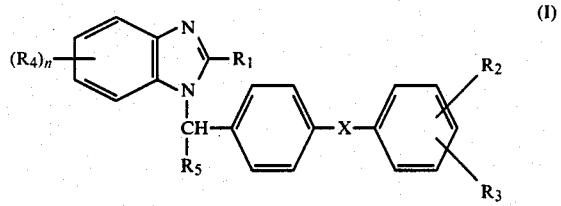

wherein $R_1$ is a hydrogen atom, a lower alkyl group or a halo(lower)alkyl group, $R_2$ and $R_3$ are, the same or different, each a hydrogen atom, a halogen atom, a nitro group, a cyano group or an optionally substituted lower alkyl, lower alkenyl, lower alkynyl, cyclo(lower)alkyl, lower alkoxy, lower alkenyloxy, lower alkynyloxy, cyclo(lower)alkoxy, lower alkylthio, lower alkenylthio, lower alkynylthio, cyclo(lower)alkylthio, di(lower)alkylamino, lower alkylsulfonyl or lower alkylsulfinyl group, or $R_2$ and $R_3$ are combined together to form an optionally substituted 5- or 6-membered, saturated or unsaturated ring optionally having not more than two oxygen or sulfur atoms in the ring, $R_4$ is a halogen atom or a lower alkyl group, $R_5$ is a hydrogen atom or a lower alkyl group, X is an oxygen atom, a sulfur atom, a methylene group, a sulfonyl group, a sulfinyl group or an imino group and n is an integer of 1 to 4, and their production and use as insecticides and/or acaricides.

The term "lower" as hereinabove used is intended to mean usually a group having not more than 12 carbon atoms, preferably not more than 8 carbon atoms and in some cases, more preferably not more than 6 carbon atoms. Specifically, $R_1$ represents a hydrogen atom, a methyl group, an ethyl group, an n-propyl group, an isopropyl group, fluoromethyl group, a difluoromethyl group, a trifluoromethyl group, a tetrafluoroethyl group, etc.; $R_2$ and $R_3$ represent each a hydrogen atom, a halogen atom, a $C_1$–$C_8$ alkyl group, a $C_2$–$C_6$ alkenyl group, a $C_2$–$C_6$ alkynyl group, a cyclo($C_3$–$C_6$)alkyl group, a $C_1$–$C_6$ alkoxy group, a $C_2$–$C_6$ alkenyloxy group, a $C_2$–$C_6$ alkynyloxy group, a cyclo($C_3$–$C_6$)alkyloxy group, a $C_2$–$C_6$ alkylthio group, a $C_2$–$C_6$ alkenylthio group, a $C_2$–$C_6$ alkynylthio group, a cyclo($C_3$–$C_6$)alkylthio group, a di($C_1$–$C_6$)alkylamino group, a $C_1$–$C_6$ alkylsulfonyl group, a $C_1$–$C_6$ alkylsulfinyl group, a halo($C_1$–$C_6$)alkyl group, a halo($C_2$–$C_6$)alkenyl group, a halo($C_2$–$C_6$)alkynyl group, a halo($C_1$–$C_6$)alkoxy group, a halo($C_2$–$C_6$)alkenyloxy group, a halo($C_2$–$C_6$)alkynyloxy group, a halo($C_1$–$C_6$)alkylthio group, a halo($C_2$–$C_6$)alkenylthio group, a halo($C_2$–$C_6$)alkynylthio group, a halo($C_1$–$C_6$)alkylsulfonyl group, a halo($C_1$–$C_6$)alkylsulfinyl group, a $C_1$–$C_6$ alkoxy($C_1$–$C_6$)alkyl group, a halo($C_1$–$C_6$)alkoxy($C_1$–$C_6$)alkyl group, a $C_1$–$C_6$ alkylthio($C_1$–$C_6$)alkyl group, a halo($C_1$–$C_6$)alkylthio($C_1$–$C_6$)alkyl group, a $C_1$–$C_6$ alkoxy($C_1$–$C_6$)alkoxy group, a halo($C_1$–$C_6$)alkoxy($C_1$–$C_6$)alkoxy group, a $C_2$–$C_6$ alkenyloxy($C_1$–$C_6$)alkyl group, a $C_2$–$C_6$ alkynyloxy($C_1$–$C_6$)alkyl group, a $C_2$–$C_6$ alkenyloxy($C_1$–$C_6$)alkoxy group, a $C_2$–$C_6$ alkynyloxy($C_1$–$C_6$)alkoxy group, a $C_1$–$C_6$ alkoxy($C_1$–$C_6$)alkylthio group, a $C_1$–$C_6$ alkylthio($C_1$–$C_6$)alkylthio group, a $C_1$–$C_6$ alkylthio($C_1$–$C_6$)alkoxy group, a 3,4-methylenedioxy group, a 3,4-difluoromethylenedioxy group, a 3,4-trifluoroethylenedioxy group, a 3,4-trimethylene group, a 3,4-tetramethylene group, etc.; $R_4$ represents a methyl group, an ethyl group, an n-propyl group, an isopropyl group, a fluorine atom, a chlorine atom, a bromine atom, etc.; and $R_5$ represents a hydrogen atom, a methyl group, an ethyl group, an n-propyl group, an isopropyl group, etc.

Among the benzimidazoles (I), preferred are those wherein $R_1$ is a hydrogen atom, a methyl group or a trifluoromethyl group, $R_2$ and $R_3$ are, the same or different, each a hydrogen atom, a halogen atom, a $C_1$–$C_8$ alkyl group, a $C_1$–$C_6$ alkoxy group or a $C_1$–$C_6$ alkylthio group, or $R_2$ and $R_3$ may be combined together to represent a 3,4-methylenedioxy group, $R_4$ is a halogen atom or a methyl group, $R_5$ is a hydrogen atom or a methyl group and X is an oxygen atom, a sulfur atom, a methylene group or a sulfonyl group. More preferred are those wherein $R_1$ is a methyl group, $R_5$ is a hydrogen atom and X is an oxygen atom.

It has been known that certain benzimidazole derivatives such as 1-(3,7-dimethylocta-2,6-dienyl)benzimidazole exhibit an insecticidal activity against house flies (Agric.Biol.Chem., 46 (6) 1715 (1982)). However, their insecticidal effect is not necessarily sufficient.

It has now been found that the benzimidazoles (I) of the present invention exhibit an excellent insecticidal activity against Diptera (e.g. common mosquito, yellow fever mosquito). It has also been found that they exhibit a prominent acaricidal activity against Tetranychidae (e.g. carmine spider mite, citrus red mite). Advantageously, their acaricidal activity is effective for Tetranychidae having resistance to conventional acaricides. The benzimidazoles (I) are thus useful as the active ingredients for agricultural insecticides, agricultural acaricides, sanitary insecticides, etc.

The benzimidazoles (I) of the present invention can be prepared by various procedures, of which typical examples are shown below:

Procedure A

The benzimidazole (I) is obtained by reacting a benzimidazole compound of the formula:

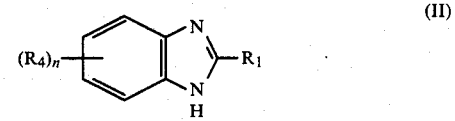

wherein $R_1$, $R_4$ and n are each as defined above with a substituted benzyl compound of the formula:

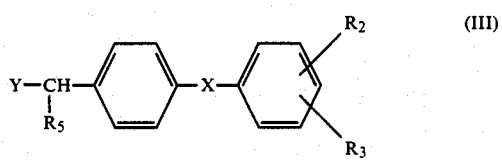

wherein $R_2$, $R_3$, $R_5$ and X are each as defined above and Y is a leaving group such as a halogen atom, a tosyloxy group or a mesyloxy group in the existence of an acid binding agent.

The molar ratio of the benzimidazole compound (II) and the substituted benzyl compound (III) is usually 1:0.1–10, normally 1:0.8–1.0. The molar ratio of the benzimidazole compound (II) and the acid binding agent may be ordinarily 1:0.9–1.1.

Examples of the acid binding agent are alkali metals (e.g. lithium, sodium, potassium), alkali metal hydrides (e.g. sodium hydride, potassium hydride), alkali metal amides (e.g. sodium amide), alkali metal hydroxides (e.g. sodium hydroxide, potassium hydroxide), alkali metal carbonates (e.g. sodium carbonate, potassium carbonate), organic bases (e.g. triethylamine, N,N-dimethylaniline, N,N-diethylaniline), etc.

The reaction may be carried out in the presence or absence of an inert solvent, preferably in the presence of an inert solvent. The reaction is generally effected at a temperature of −30° C. to the boiling temperature of the reaction mixture, preferably from 0° to 110° C. The reaction is usually accomplished within a period of 0.5 to 50 hours.

Examples of the inert solvent are water, hydrocarbons (e.g. benzene, toluene, xylene), ethers (e.g. diethyl ether, diisopropyl ether, dioxane, tetrahydrofuran, ethylene glycol dimethyl ether, dimethoxyethane), ketones (e.g. acetone, methylethylketone, methylisobutylketone, cyclohexanone), acid amides (e.g. dimethylformamide, diethylformamide, dimethylacetamide) and sulfoxides (e.g. dimethylsulfoxide), and their mixtures.

In order to accelerate the reaction, a phase transfer catalyst such as benzyltriethylammonium chloride or tetrabutylammonium bromide may be employed.

The reaction mixture is usually subjected to a post-treatment such as extraction with a solvent and concentration. When desired, the product may be purified by a per se conventional procedure such as column chromatography, distillation or recrystallization.

Procedure B

The benzimidazole (I) is obtained by reacting a carboxylic acid compound of the formula:

wherein $R_1$ is as defined above, or its reactive derivative, with an aniline compound of the formula:

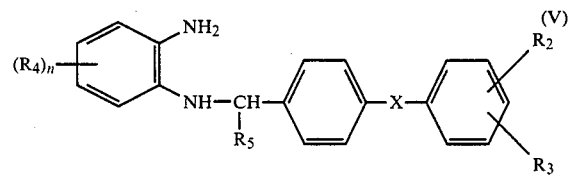

wherein $R_2$, $R_3$, $R_4$, $R_5$, X and n are each as defined above.

The molar ratio of the aniline compound (V) and the carboxylic acid compound (IV) or its reactive derivative is usually from 1:1–100, normally from 1:1–10.

As the reactive derivative of the carboxylic acid compound (IV), there may be exemplified carboxylic acid anhydride, orth-carboxylic acid ester, carboxylic acid halide, carboxylic acid ester, etc. The reaction may be carried out in the presence or absence of an inert solvent, of which preferred examples are water, benzene, toluene, carbon tetrachloride, chloroform and ethylene chloride, and their mixtures. The reaction temperature is from 25 to 200° C., generally from 50° C. to the boiling temperature of the reaction mixture. The reaction may be usually accomplished within a period of 1 to 50 hours.

The reaction mixture is usually subjected to a post-treatment such as extraction with a solvent and concentration. When desired, the product may be purified by a per se conventional procedure such as column chromatography, distillation or recrystallization.

Procedure C

The benzimidazole (I) is obtained by subjecting an anilide compound of the formula:

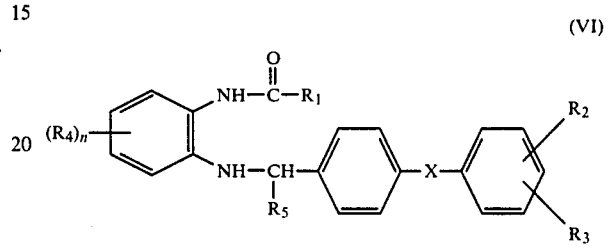

wherein $R_1$, $R_2$, $R_3$, $R_4$, $R_5$, X and n are each as defined above to ring closure in the presence of an acid catalyst in an inert organic solvent.

As the acid catalyst, there may be employed sulfuric acid, p-toluenesulfonic acid, benzenesulfonic acid, carboxylic acids, etc.

Preferred examples of the solvent are benzene, toluene, xylene, o-dichlorobenzene, chloroform, carbon tetrachloride, etc. The carboxylic acid of the formula:

wherein $R_1$ is as defined above may be also used as the solvent. In this case, the carboxylic acid itself can play a role as the acid catalyst.

The reaction temperature may be in general from room temperature to the boiling point of the reaction mixture. Separation or removal of water from the reaction system is effective in accelerating the reaction.

The reaction mixture is usually subjected to a post-treatment such as extraction with a solvent and concentration. When desired, the product may be purified by a per se conventional procedure such as column chromatography, distillation or recrystallization.

As the benzimidazole compound (II), there may be exemplified 4-methylbenzimidazole, 2,4-dimethylbenzimidazole, 4-chloro-2-methylbenzimidazole, 4-fluorobenzimidazole, 5-chloro-2-methylbenzimidazole, 5,6-dichloro-2-methylbenzimidazole, 4-fluoro-2-methylbenzimidazole, 4,6-dichloro-2-methylbenzimidazole, 4-bromo-2-methylbenzimidazole, 4-chloro-2-n-propylbenzimidazole, 2-ethyl-4-methylbenzimidazole, 4-chloro-2-trifluoromethylbenzimidazole, 4-methyl-2-isopropylbenzimidazole, 4-methyl-2-trifluoromethylbenzimidazole, etc.

The substituted benzyl compound (III) is per se known or may be prepared by a conventional process. Examples of the substituted benzyl compound (III) are 4-phenoxybenzyl bromide, 4-(3-tolyloxy)benzyl chloride, 4-(4-n-pentylphenoxy)benzyl chloride, 4-(4-ethoxyphenoxy)benzyl chloride, 4-(3-ethoxyphenoxy)benzyl chloride, 4-(4-methylthiophenoxy)benzyl chloride, 4-benzoylbenzyl bromide, 4-(4-vinyloxyphenoxy)benzyl chloride, 4-(3-chlorophenoxy)benzyl chloride, 4-(2-fluorophenoxy)benzyl p-toluenesulfonate, 4-(3-fluorophenoxy)benzyl bromide, 4-(3-isopropylphenoxy)benzyl chloride, 4-(4-ethynylphenoxy)benzyl chloride, 4-(3-n-propylthiophenoxy)benzyl chloride, 4-(4-methanesulfonylphenoxy)benzyl chloride, 4-(3-trifluoromethylphenoxy)benzyl bromide, 4-(4-cyclopropylphenoxy)benzyl chloride, 4-(2-chlorophenylthio)benzyl bromide, 4-(3-bromophenoxy)benzyl bromide, 4-(4-ethylphenoxy)benzyl chloride, 4-(3-ethylphenoxy)benzyl chloride, 4-(3-N,N-dimethylaminophenoxy)benzyl bromide, 4-(3-n-propoxyphenoxy)benzyl chloride, 4-(3-n-butoxyphenoxy)benzyl chloride, 4-(3-n-pentyloxyphenoxy)benzyl chloride, 4-(4-isopropylthiophenoxy)benzyl chloride, 4-[4-(2,2-dichlorovinyl)phenoxy]benzyl chloride, 4-(3-n-propylphenoxy)benzyl chloride, 4-(4-isopropylphenoxy)benzyl chloride, 4-benzylbenzyl methanesulfonate, 4-(3-ethylthiophenoxy)benzyl chloride, 4-(4-methoxymethylphenoxy)benzyl chloride, 1-[4-(4-ethoxyphenoxy)phenyl]ethyl bromide, 4-(4-n-butylthiophenoxy)benzyl chloride, 4-(4-difluoromethoxyphenoxy)benzyl chloride, 4-(4-n-propylphenoxy)benzyl chloride, 4-(4-n-butylphenoxy)benzyl chloride, 4-(3-vinylphenoxy)benzyl chloride 4-(4-allylphenoxy)benzyl chloride, 4-(4-n-propoxyphenoxy)benzyl chloride, 4-(4-sec-butylphenoxy)benzyl chloride, 4-(2,5-dimethylphenoxy)benzyl chloride, 4-(2,3-dimethylphenoxy)benzyl chloride, 4-(3,5-difluorophenoxy)benzyl chloride, 4-(4-n-butoxyphenoxy)benzyl chloride, 4-(4-n-pentylthiophenoxy)benzyl chloride, 4-(3,4-methylenedioxyphenoxy)benzyl chloride, 4-(4-allylthiophenoxy)benzyl chloride, 4-(3-allyloxyphenoxy)benzyl chloride, 1-[4-(4-methylthiophenoxy)phenyl]ethyl bromide, 4-(4-propargyloxyphenoxy)benzyl chloride, 4-(4-n-hexylphenoxy)benzyl chloride, 4-[4-(2-butenyl)phenoxy]benzyl chloride, 4-[4-(1-methylallyl)phenoxy]benzyl chloride, 4-(3-n-hexyloxyphenoxy)benzyl chloride, 4-(3-isopropoxyphenoxy)benzyl chloride, 4-[4-(1-methylcyclopropyl)phenoxy]benzyl chloride, 4-(3-ethynyloxyphenoxy)benzyl chloride, 4-(4-allylthiophenoxy)benzyl chloride, 4-[4-(2,2-dichlorovinyloxy)phenoxy]benzyl chloride, 4-[4-(2-chloroallyl)phenoxy]benzyl chloride, 4-[4-(1,1,2,2-tetrafluoroethoxy)phenoxy]benzyl chloride, 4-(3-chloro4-methylphenoxy)benzyl chloride, 4-(3,4-difluoromethylenedioxyphenoxy)benzyl chloride, 1-[4-(4-chloro-3-methylphenoxy)phenyl]ethyl bromide, 4-(4-sec-pentylphenoxy)benzyl chloride, 4-[4-(2-methylallyl)phenoxy]benzyl chloride, 4-[4-(2-chloroethynyl)phenoxy]benzyl chloride, 4-(4-methoxymethylthiophenoxy)benzyl chloride, 4-[4-(2,2,2-trifluoroethoxy)phenoxy]benzyl chloride, 4-(4-ethoxymethylphenoxy)benzyl chloride, 4-(3-trifluoromethylthiophenoxy)benzyl chloride, 4-(3-methoxy-4-methylphenoxy)benzyl chloride, 4-(4-propargylphenoxy)benzyl chloride, 4-(4-ethyl-2-methylphenoxy)benzyl chloride, 4-(2-methyl-4-n-propylphenoxy)benzyl chloride, 4-(4-n-butyl-2-methylphenoxy)benzyl chloride, 4-[4-(1-methyl-2-butenyl)phenoxy]benzyl chloride, 4-(3-methoxyphenoxy)benzyl chloride, 1-[4-(4-ethoxyphenoxy)phenyl]propyl bromide, 4-(4-isopropoxyphenoxy)benzyl chloride, 4-(4-sec-butoxyphenoxy)benzyl chloride, 4-(4-n-pentyloxyphenoxy)benzyl chloride, 4-[4-(1-ethoxyethyl)phenoxy]benzyl chloride, 4-(3-allylthiophenoxy)benzyl chloride, 4-(4-cyclopropylthiophenoxy)benzyl chloride, 4-(3-allyloxymethylphenoxy)benzyl chloride, 4-(4-ethoxyphenylthio)benzyl chloride, 4-(3-ethynyloxymethylphenoxy)benzyl chloride, 4-(4-methylthiomethylthiophenoxy)benzyl chloride, 4-(4-isobutylthiophenoxy)benzyl chloride, 4-[4-(2-methylallyloxy)phenoxy]benzyl chloride, 4-(3-ethanesulfonylphenoxy)benzyl chloride, 4-[4-(1,1-dichloro-2,2-difluoroethoxy)phenoxy]benzyl chloride, 4-(2-methyl-4-n-propoxyphenoxy)benzyl chloride, 4-(2-chloro-4-ethoxyphenoxy)benzyl chloride, 4-[4-(2-butenyloxy)phenoxy]benzyl chloride, 4-[4-(1-methylallyloxy)phenylthio]benzyl chloride, 4-(3-ethoxyanilino)benzyl chloride, 4-(5,6,7,8-tetrahydro-2-naphthyloxy)benzyl chloride, 4-(4-bromo-3-chlorophenoxy)benzyl chloride, 4-(4-trifluoromethylphenoxy)benzyl chloride, 4-benzenesulfinylbenzyl bromide, 4-(3-nitrophenoxy)benzyl chloride, 4-(4-n-propoxyphenoxy)benzyl chloride, 4-(4-methoxyphenoxy)benzyl chloride, 4-(4-ethylthiophenoxy)benzyl chloride, 4-(4-n-propylthiophenoxy)benzyl chloride, 4-(3-methylthiophenoxy)benzyl chloride, 4-(3-n-butylthiophenoxy)benzyl chloride, 4-(4-n-propoxyphenylthio)benzyl chloride, 4-(4-ethylbenzoyl)benzyl chloride, 4-(2,3-dihydrobenzofuran-5-yloxy)benzyl chloride, 4-(2,3-dihydro-2,2-dimethylbenzofuran-5-yloxy)benzyl chloride, 4-(indan-5-yloxy)benzyl chloride, 4-[4-(2,2,3-trifluoroethoxy)phenoxy]benzyl chloride, 4-]4-(2-bromo-1,1,2,2-tetrafluoroethoxy)phenoxy]benzyl chloride, etc.

The aniline compound (V) is novel and can be prepared by a per se conventional procedure. A typical example for preparation of the aniline compound (V) is schematically shown below:

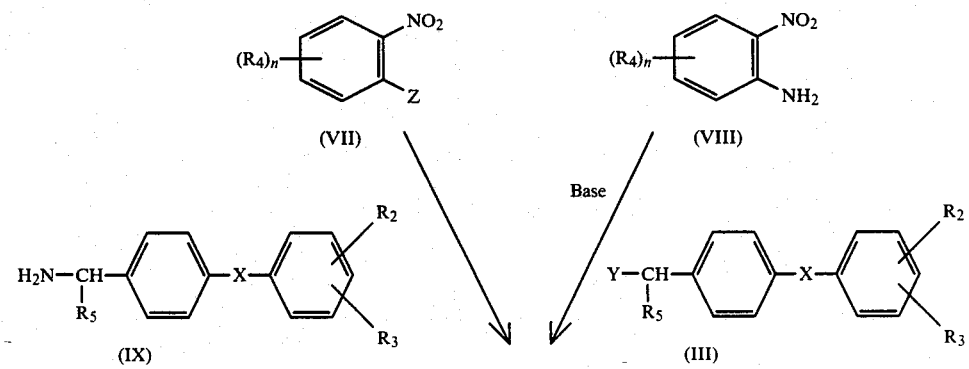

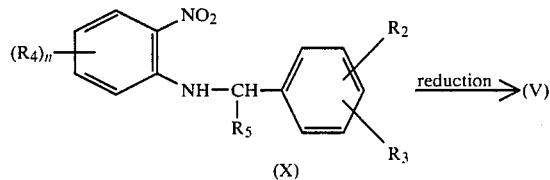

wherein $R_2$, $R_3$, $R_4$, $R_5$, X, Y and n are each as defined above and Z is a halogen atom.

The anilide compound (VI) is also novel and may be prepared, for instance, by a per se conventional procedure. A typical example is shown below:

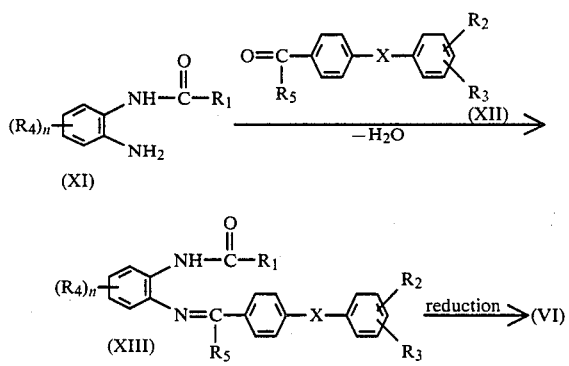

wherein $R_1$, $R_2$, $R_3$, $R_4$, $R_5$, X and n are each as defined above.

Practical and presently preferred embodiments for preparation of the benzimidazole (I) are illustratively shown in the following Examples.

EXAMPLE 1

To a mixture of anhydrous N,N-dimethylforamide (10 ml) and sodium hydride (62% oil suspension; 0.071 g), 4-chloro-2-methylbenzimidazole (0.304 g) was added while stirring, and the stirring was continued at room temperature for 1 hour. The resultant mixture was cooled to 5°–10° C., and a solution of 4-(4-ethoxyphenoxy)benzyl chloride (0.400 g) in anhydrous N,N-dimethylformaide (10 ml) was dropwise added thereto in 30 minutes, followed by stirring at room temperature overnight. After completion of the reaction, the reaction mixture was poured into water (100 ml) and extracted with toluene (30 ml) two times. The toluene extract was washed with water, dried over anhydrous sodium sulfate and distilled under reduced pressure to remove toluene. The residue was purified by silica gel column chromatography to give 4-chloro-1-[4-(4-ethoxyphenoxy)benzyl]-2-methylbenzimidazole (0.204 g) as a colorless liquid. $n_D^{26.5}$ 1.6087.

From the second fraction, there was obtained 7-chloro-1-[4-(4-ethoxyphenoxy)benzyl]-2-methylbenzimidazole (0.020 g) as a colorless liquid. $n_D^{22.5}$ 1.6103.

EXAMPLE 2

A mixture of 3-chloro-2-(4-phenoxybenzylamino)aniline (0.300 g) and ethyl ortho-formate (0.178 g) was heated at 120° to 130° C. for 5 hours while stirring and then cooled to room temperature. Toluene (100 ml) and a 5% sodium hydroxide solution (50 ml) were added thereto, followed by stirring for 10 minutes. The toluene layer was separated and washed with water, dried over anhydrous sodium sulfate and distilled under reduced pressure to remove toluene. The residue was purified by silica gel column chromatography to give 7-chloro-1-(4-phenoxybenzyl)benzimidazole (0.239 g) as a colorless liquid. $n_D^{28.5}$ 1.6362.

EXAMPLE 3

A mixture of 2-[4-(4-ethoxyphenoxy)benzylamino)-3-methylaniline (0.348 g) and acetic acid (5 ml) was heated under reflux for 6 hours and then cooled to room temperature. Excess acetic acid was removed by distillation under reduced pressure, and toluene (100 ml) and a 5% sodium hydroxide solution (50 ml) were added thereto, followed by stirring for 10 minutes. The toluene layer was separated, washed with water, dried over anhydrous sodium sulfate and distilled under reduced pressure to remove toluene. The residue was purified by silica gel column chromatography to give 2,7-dimethyl-1-[4-(4-ethoxyphenoxy)benzyl]benzimidazole (0.315 g) as white crystals. m.p., 124.1° C.

EXAMPLE 4

A mixture of 2-acetamido-1-chloro-3-[4-(4-methylthiophenoxy)benzylamino]benzene (0.413 g), p-toluenesulfonic acid (0.040 g) and toluene (150 ml) was heated under reflux while removing the by-produced water therefrom through a Dean-Stark trap. After the by-production of water ceased, the reaction mixture was cooled to room temperature, washed with a saturated sodium carbonate solution and water and distilled under reduced pressure to remove toluene. The residue was purified by silica gel column chromatography to give 4-chloro-2-methyl-1-[4-(4-methylthiophenoxy)benzyl]-benzimidazole (0.375 g) as a colorless liquid. $n_D^{22.0}$ 1.6341.

In the same manner as above, the benzimidazoles (I) as shown in Table 1 were obtained.

TABLE 1

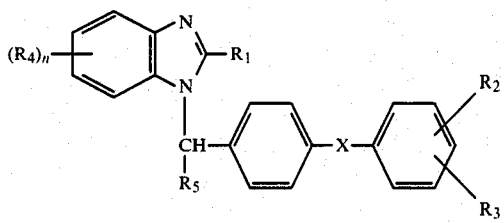

| Compound No. | $R_1$ | $R_2$ | $R_3$ | $(R_4)_n$ | $R_5$ | X | Physical constant |
|---|---|---|---|---|---|---|---|
| 1 | $CH_3$ | H | H | 4-Cl | H | O | $n_D^{25.5}$ 1.6048 |
| 2 | $CH_3$ | H | H | 4-$CH_3$ | H | O | $n_D^{28.0}$ 1.6225 |
| 3 | $CH_3$ | H | H | 7-Cl | H | O | $n_D^{28.5}$ 1.6258 |
| 4 | H | H | H | 7-Cl | H | O | $n_D^{28.5}$ 1.6362 |
| 5 | $CH_3$ | H | H | 7-$CH_3$ | H | O | m.p. 108–112° C. |
| 6 | H | H | H | 7-$CH_3$ | H | O | $n_D^{20.5}$ 1.6236 |
| 7 | $CH_3$ | 4-$OC_2H_5$ | H | 4-Cl | H | O | $n_D^{26.5}$ 1.6087 |
| 8 | $CH_3$ | 4-$OC_2H_5$ | H | 4-$CH_3$ | H | O | $n_D^{24.5}$ 1.6027 |
| 9 | $CH_3$ | H | H | 6-Cl | H | O | m.p. 127.4° C. |
| 10 | $CH_3$ | 4-$OCH_2CH=CH_2$ | H | 4-$CH_3$ | H | O | $n_D^{25.0}$ 1.6157 |
| 11 | $CH_3$ | 4-$OC_2H_5$ | H | 7-Cl | H | O | $n_D^{25.5}$ 1.6103 |
| 12 | $CH_3$ | 4-$OC_2H_5$ | H | 7-$CH_3$ | H | O | m.p. 124.1° C. |
| 13 | H | 4-$OC_2H_5$ | H | 7-$CH_3$ | H | O | m.p. 78–82° C. |
| 14 | $CH_3$ | 3-F | 5-F | 4-Cl | H | O | $n_D^{25.0}$ 1.6105 |
| 15 | $CH_3$ | 3-$CH_3$ | 4-Cl | 4-Cl | H | O | $n_D^{23.0}$ 1.6296 |
| 16 | $CH_3$ | 4-$C_2H_5$ | H | 4-Cl | H | O | $n_D^{24.0}$ 1.6212 |
| 17 | $CH_3$ | 3,4-(O—$CH_2$—O—) | | 4-Cl | H | O | $n_D^{25.0}$ 1.6260 |
| 18 | $CH_3$ | H | H | 4-Cl | H | S | $n_D^{23.5}$ 1.6546 |
| 19 | $CH_3$ | 3-Cl | H | 4-Cl | H | O | $n_D^{23.0}$ 1.6309 |
| 20 | $CH_3$ | 4-$C_3H_7$(n) | H | 4-Cl | H | O | $n_D^{23.5}$ 1.6081 |
| 21 | $CH_3$ | 4-$SCH_3$ | H | 4-Cl | H | O | $n_D^{22.0}$ 1.6341 |
| 22 | $CH_3$ | 4-$OC_2H_5$ | H | 4-Br | H | O | Glassy |
| 23 | $CH_3$ | 4-$OC_2H_5$ | H | 4-F | H | O | $n_D^{23.5}$ 1.5998 |
| 24 | $CH_3$ | 3-F | 5-F | 4-$CH_3$ | H | O | m.p. 202.0° C. |
| 25 | $CH_3$ | 4-$SCH_3$ | H | 4-$CH_3$ | H | O | $n_D^{24.0}$ 1.6410 |
| 26 | $CH_3$ | 4-$C_2H_5$ | H | 4-$CH_3$ | H | O | $n_D^{24.0}$ 1.6104 |
| 27 | $CH_3$ | 3-$CH_3$ | 4-Cl | 4-$CH_3$ | H | O | $n_D^{27.0}$ 1.6145 |
| 28 | $CF_3$ | 4-$OC_2H_5$ | H | 4-$CH_3$ | H | O | $n_D^{24.0}$ 1.5754 |
| 29 | $CH_3$ | 3-$CH_3$ | H | 4-$CH_3$ | H | O | $n_D^{24.0}$ 1.6160 |
| 30 | $CH_3$ | 4-$OC_2H_5$ | H | 4-$CH_3$ | $CH_3$ | O | $n_D^{21.5}$ 1.6048 |
| 31 | $CH_3$ | 4-$OC_2H_5$ | H | 4-Cl | $CH_3$ | O | $n_D^{24.5}$ 1.6080 |
| 32 | $CH_3$ | 4-$C_2H_5$ | H | 4-$CH_3$ | H | $CH_2$ | $n_D^{24.0}$ 1.6247 |
| 33 | $CH_3$ | 4-$C_2H_5$ | H | 4-$CH_3$ | H | NH | $n_D^{21.5}$ 1.6195 |
| 34 | $CH_3$ | 4-$C_2H_5$ | H | 4-$CH_3$ | H | SO | $n_D^{23.5}$ 1.6649 |
| 35 | $CH_3$ | 4-$C_2H_5$ | H | 4-$CH_3$ | H | $SO_2$ | $n_D^{24.5}$ 1.6628 |
| 36 | $CH_3$ | 4-$SCH_3$ | H | 4.7-$Cl_2$ | H | O | $n_D^{23.5}$ 1.6345 |

In the application of the benzimidazoles (I) as insecticidal and/or acaricidal agents, they may be used as such or in the form of appropriate compositions such as emulsifiable concentrates, wettable powders, dusts, granules, oils, aerozoles, heating or non-heating fumigants, sprays, baits, etc. The content of the benzimidazoles (I) in there compositions is usually from about 0.01 to 95% by weight.

The composition can be formulated in a per se conventional manner by mixing at least one of the benzimidazoles (I) with an appropriate solid, liquid or gaseous carrier(s) or diluent(s). An appropriate adjuvant(s) (e.g. surfactants, adherents, dispersants, stabilizers) may be also mixed therein for improving the dispersibility and other properties of the composition.

Examples of the solid carriers or diluents are kaolin clay, attapulgite clay, bentonite, fuller's earth, pyrophyllite, talc, diatomaceous earth, calcite, corn stem powders, walnut-shell powders, fine powders or granules of urea, ammonium sulfate or synthetic hydrated silica, etc. Examples of the liquid carriers or diluents are aliphatic hydrocarbons (e.g. kerosene, lamp oil), aromatic hydrocarbons (e.g. benzene, toluene, xylene, methylnaphthalene), halogenated hydrocarbons (e.g. dichloroethane, trichloroethylene, carbon tetrachloride), alcohols (e.g. methyl alcohol, ethyl alcohol isopropyl alcohol, ethylene glycol, cellosolve), ketones (e.g. acetone, methylethylketone, cyclohexanone, isophorone), ethers (e.g. diethyl ether, dioxane, tetrahydrofuran), esters (e.g. ethyl acetate), nitriles (e.g. acetonitrile, isobutyronitrile), acid amides (e.g. dimethylformamide, dimethylacetamide), dimethylsulfoxide, botanical oils (e.g. soybean oil, cotton-seed oil), etc. Examples of the gaseous carriers or diluents are Freon gas, LPG (liquefied petroleum gas), dimethyl ether, etc.

Examples of the surfactants used for emulsification, dispersion or spreading may be any of ionic and non-ionic types. Examples of the ionic surfactants are alkylsulfates, alkylsulfonates, arylsulfonates, dialkylsulfosuccinates, phosphates of polyoxyethylene alkylaryl ether, condensates of naphthalenesulfonic acid and formalin, etc. Examples of the non-ionic surfactants are polyoxyethylene alkyl ethers, polyoxyethylene polyoxypropylene blocked copolymers, sorbitan fatty acid esters, polyoxyethylene sorbitan fatty acid esters, etc. Examples of the adherents and dispersants may include ligninsulfonates, alginates, polyvinyl alcohol, gum arabic, mollasses, casein, gelatin, CMC (carboxymethyl cellulose), pine seed oil, agar, etc. As the stabilizers, there may be used alkyl phosphates (e.g. PAP (isopropyl acid phosphate), TCP (tricresyl phosphate)), botanical oils, epoxidized oils, various surfactants, antioxidizing agents (e.g. BHT (2,6-di-t-butyl-p-cresol), BHA (mixture of 2-t-butyl-4-methoxyphenol and 3-t-butyl-4-methoxyphenol)), aliphatic acid salts (e.g. sodium oleate, calcium stearate), aliphatic acid esters (e.g. methyl oleate, methyl stearate), etc.

The benzimidazoles (I) of the present invention formulated into an appropriate composition may be applied as such or in a form of dilution with water by a suitable application method such as spraying, fumigating or smoking, or in combination with an animal bait.

In addition, the composition may contain other insecticides, acaricides, nematocides, fungicides, herbicides, plant growth regulators, fertilizers, soil improvers, etc.

The dosage of the benzimidazole (I) as the active ingredient in an insecticidal and/or acaricidal composition is generally from 5 to 500 grams per 10 ares. When the composition is applied as an emulsifiable concentrate or a wettable powder, the concentration of the active ingredient may be normally from 10 to 1000 ppm. In case of such formulation as dusts, granules, oils, aerosoles, etc., the composition may be applied as such without diluting with water.

Some practical embodiments of the composition for the control of insects and/or acarids according to the present invention are illustratively shown in the following Formulation Examples wherein % and part(s) are by weight.

FORMULATION EXAMPLE 1

Compound No. 9 (0.2 part), xylene (2 parts) and lamp oil (97.8 parts) are mixed well to make an oil.

FORMULATION EXAMPLE 2

Anyone of Compound Nos. 1 to 36 (10 parts), polyoxyethylene styrylphenyl ether (14 parts), calcium dodecylbenzenesulfonate (6 parts), xylene (35 parts) and N,N-dimethylformamide (35 parts) are mixed well to make an emulsifiable concentrate.

FORMULATION EXAMPLE 3

Compound No. 7, 8 or 11 (20 parts), fenitrothion (O,O-dimethyl-O-(3-methyl-4-nitrophenyl)phosphorothioate) (10 parts), calcium ligninsulfonate (3 parts), sodium laurylsulfate (2 parts) and synthetic hydrated silica (65 parts) are mixed well in a pulverizer to make a wettable powder.

FORMULATION EXAMPLE 4

Compound No. 8, 12 or 15 (1 part), carbaryl (1-naphthyl N-methylcarbamate) (2 parts), kaolin clay (87 parts) and talc (10 parts) are mixed well in a pulverizer to give a dust.

FORMULATION EXAMPLE 5

Compound No. 8 or 27 (5 parts), synthetic hydrated silica (1 part), calcium ligninsulfonate (2 parts), bentonite (30 parts) and kaolin clay (62 parts) are mixed well in a pulverizer. To the resultant mixture, water is added, and the resulting mixture is kneaded well and granulated by the aid of a granulator, followed by drying to give granules.

The following Test Examples present some typical test data indicating the excellent insecticidal and acaricidal activities of the benzimidazoles (I). The compounds used for comparison are as follows:

| Compound No. | Chemical structure | Remarks |
|---|---|---|
| A | benzimidazole with $CH_2CH=C(CH_3)-CH_2CH_2CH=C(CH_3)_2$ substituent | Agric. Biol. Chem., 46, (6) 1715 (1982) |
| B | $Cl-C_6H_3(CH_3)-N=CH-N(CH_3)_2$ | Chlorodimeform |
| C | $(Cl-C_6H_4)_2C(OH)(CCl_3)$ | Dicofol |

TEST EXAMPLE 1

An emulsifiable concentrate prepared as in Formulation Example 2 was diluted with water to make a concentration of 3.5 ppm. The dilution (100 ml) was charged in a plastic cup (each 180 ml volume), and twenty last instar larvae of common mosquito (*Culex pipiens pallens*) were released therein. On the next day, the rate of death was calculated. Thereafter, the feeding was continued until all the larvae in the untreated plot emerged, whereupon the rate of emergence inhibition was observed.

The rate of death and the rate of emergence inhibition were respectively determined according to the following criteria:

Rate of death
a: more than 90% death
b: between 90 and 10% death
c: less than 10% death Rate of emergence inhibition
a: more than 90% inhibition
b: between 90 and 80% inhibition
c: less than 80% inhibition The results are shown in Table 2.

TABLE 2

| Compound No. | Rate of death | Rate of emergence inhibition |
|---|---|---|
| 1 | b | a |
| 2 | b | a |
| 8 | a | a |
| 9 | b | a |
| 17 | b | a |
| 18 | b | a |
| 21 | b | a |
| 22 | b | a |
| 23 | c | a |
| 24 | a | a |
| 25 | b | a |
| 26 | b | a |
| 27 | b | a |
| 28 | c | b |
| 29 | a | a |
| Untreated | c | c |

TEST EXAMPLE 2

Adults of female carmine spider mites (*Tetranychus cinnabarinus*) were permitted to live on leaves (10 mites per leaf) of kidney bean after 7 days of its plantation in the pots, and the adults were kept at 25° C. After 6 days, a dilution (500 ppm) of the emulsifiable concentrate prepared as in Formulation Example 2 was sprayed over the pots placed on a turn table at a spray volume of 10 ml per pot, and also 2 ml of the dilution were applied to the soil in each pot. Eight days thereafter, the plant damage by the mites was observed and evaluated according to the following criteria:

−: no material damage to leaves
+: slight damage to leaves
++: same damage as seen in untreated plot The results are shown in Table 3.

TABLE 3

| Compound No. | Plant damage |
|---|---|
| 1 | − |
| 2 | −~+ |
| 3 | −~+ |
| 4 | −~+ |
| 5 | − |
| 6 | −~+ |
| 7 | − |
| 8 | − |
| 10 | −~+ |
| 11 | − |
| 12 | − |
| 13 | −~+ |
| 14 | − |
| 15 | − |
| 16 | − |
| 17 | − |
| 18 | − |
| 19 | − |
| 20 | − |
| 21 | − |
| 22 | − |
| 23 | − |
| 24 | − |
| 25 | − |
| 26 | − |
| 27 | −~+ |
| 28 | − |
| 29 | − |
| 30 | − |
| 31 | − |
| 32 | −~+ |
| 33 | −~+ |
| 34 | −~+ |
| 35 | −~+ |
| 36 | −~+ |
| A | ++ |
| B | + |
| C | −~+ |
| Untreated | ++ |

What is claimed is:
1. A compound of the formula:

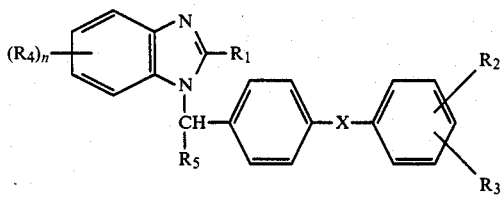

wherein $R_1$ is a hydrogen atom, a lower alkyl group or a halo(lower)alkyl group, $R_2$ and $R_3$ are, the same or different, each a hydrogen atom, a halogen atom, a nitro group, a cyano group, a lower alkyl group, a lower alkyl group substituted with a member selected from the group consisting of halogen, lower alkoxy, halo(lower)alkoxy, lower alkylthio, halo(lower)alkylthio, lower alkenyloxy and lower alkynyloxy, a lower alkenyl group, a lower alkenyl group substituted with a member selected from the group consisting of halogen, lower alkoxy, halo(lower)alkoxy, lower alkylthio, halo(lower)alkylthio, lower alkenyloxy and lower alkynyloxy, a lower alkynyl group, a lower alkynyl group substituted with a member selected from the group consisting of halogen, lower alkoxy, halo(lower)alkoxy, lower alkylthio, halo(lower)alkylthio, lower alkenyloxy and lower alkynyloxy, a cyclo(lower)alkyl group, a cyclo(lower)alkyl group substituted with a member selected from the group consisting of halogen, lower alkoxy, halo(lower)alkoxy, lower alkylthio, halo(lower)alkylthio, lower alkenyloxy and lower alkynyloxy, a lower alkoxy group, a lower alkoxy group substituted with a member selected from the group consisting of halogen, lower alkoxy, halo(lower)alkoxy, lower alkylthio, halo(lower)alkylthio, lower alkenyloxy and lower alkynyloxy, a lower alkenyloxy group, a lower alkenyloxy group substituted with a member selected from the group consisting of halogen, lower alkoxy, halo(lower)alkoxy, lower alkylthio, halo(lower)alkylthio, lower alkenyloxy and lower alkynyloxy, a lower alkynyloxy group, a lower alkynyloxy group substituted with a member selected from the group consisting of halogen, lower alkoxy, halo(lower)alkoxy, lower alkylthio, halo(lower)alkylthio, lower alkenyloxy and lower alkynyloxy, a cyclo(lower)alkoxy group, a cyclo(lower)alkoxy group substituted with a member selected from the group consisting of halogen, lower alkoxy, halo(lower)alkoxy, lower alkylthio, halo(lower)alkylthio, lower alkenyloxy and lower alkynyloxy, a lower alkylthio group, a lower alkylthio group substituted with a member selected from the group consisting of halogen, lower alkoxy, halo(lower)alkoxy, lower alkylthio, halo(lower)alkylthio, lower alkenyloxy and lower alkynyloxy, a lower alkenylthio group, a lower alkenylthio group substituted with a member selected from the group consisting of halogen, lower alkoxy, halo(lower)alkoxy, lower alkylthio, halo(lower)alkylthio, lower alkenyloxy and lower alkynyloxy, a lower alkynylthio group, a lower alkynylthio group substituted with a member selected from the group consisting of halogen, lower alkoxy, halo(lower)alkoxy, lower alkylthio, halo(lower)alkylthio, lower alkenyloxy and lower alkynyloxy, a cyclo(lower)alkylthio group, a cyclo(lower)alkylthio group substituted with a member selected from the group consisting of halogen, lower alkoxy, halo(lower)alkoxy, lower alkylthio, halo(lower)alkylthio, lower alkenyloxy and lower alkynyloxy, a di(lower)alkylamino group, a di(lower)alkylamino group substituted with a member selected from the group consisting of halogen, lower alkoxy, halo(lower)alkoxy, lower alkylthio, halo(lower)alkylthio, lower alkenyloxy and lower alkynyloxy, a lower alkylsulfonyl group, a lower alkylsulfonyl group substituted with a member selected from the group consisting of halogen, lower alkoxy, halo(lower)alkoxy, lower alkylthio, halo(lower)alkylthio, lower alkenyloxy and lower alkynyloxy, a lower alkylsulfinyl group and a lower alkylsulfinyl group substituted with a member selected from the group consisting of halogen, lower alkoxy, halo(lower)alkoxy, lower alkylthio, halo(lower)alkylthio, lower alkenyloxy and lower alkynyloxy, or $R_2$ and $R_3$ are combined together at their terminals to form a 3,4-methylenedioxy group, a 3,4-difluoromethylenedioxy group, a 3,4-trifluoroethylenedioxy group, a 3,4-trimethylene group or a 3,4-tetramethylene group, $R_4$ is a halogen atom or a lower alkyl group, $R_5$ is a hydrogen atom or a lower alkyl group, X is an oxygen atom, a sulfur atom, a methylene group, a sulfonyl group, a sulfinyl group or an imino group and n is an integer of 1 to 4.

2. The compound according to claim 1, wherein $R_2$ and $R_3$ are, the same or different, each a $C_1$-$C_8$ alkyl group, a $C_2$-$C_6$ alkenyl group, a $C_2$-$C_6$ alkynyl group, a cyclo($C_3$-$C_6$)alkyl group, a $C_1$-$C_6$ alkoxy group, a $C_2$-$C_6$ alkenyloxy group, a $C_2$-$C_6$ alkynyloxy group, a cyclo($C_3$-$C_6$)alkyloxy group, a $C_1$-$C_6$ alkylthio group, a $C_2$-$C_6$ alkenylthio group, a $C_2$-$C_6$ alkynylthio group, a cyclo($C_3$-$C_6$)alkylthio group, a di($C_1$-$C_6$)alkylamino group, a $C_1$-$C_6$ alkylsulfonyl group, a $C_1$-$C_6$ alkylsulfinyl group, a halo($C_1$-$C_6$)alkyl group, a halo($C_2$-$C_6$)alkenyl group, a halo($C_2$-$C_6$)alkynyl group, a halo($C_1$-$C_6$)alkoxy group, a halo($C_2$-$C_6$)alkenyloxy group, a halo($C_2$-$C_6$)alkynyloxy group, a halo($C_1$-$C_6$)alkylthio group, a halo($C_2$-$C_6$)alkenylthio group, a halo($C_2$-$C_6$)alkynylthio group, a halo($C_1$-$C_6$)alkylsulfonyl group, a halo($C_1$-$C_6$)alkylsulfinyl group, a $C_1$-$C_6$ alkoxy($C_1$-$C_6$)alkyl group, a halo($C_1$-$C_6$)alkoxy($C_1$-$C_6$)alkyl group, a $C_1$-$C_6$ alkylthio($C_1$-$C_6$)alkyl group, a halo($C_1$-$C_6$)alkylthio($C_1$-$C_6$)alkyl group, a $C_1$-$C_6$ alkoxy($C_1$-$C_6$)alkoxy group, a halo($C_1$-$C_6$)alkoxy($C_1$-$C_6$)alkoxy group, a $C_2$-$C_6$ alkenyloxy($C_1$-$C_6$)alkyl group, a $C_2$-$C_6$ alkynyloxy($C_1$-$C_6$)alkyl group, a $C_2$-$C_6$ alkenyloxy($C_1$-$C_6$)alkoxy group, a $C_2$-$C_6$ alkynyloxy($C_1$-$C_6$)alkoxy group, a $C_1$-$C_6$ alkoxy($C_1$-$C_6$)alkylthio group, a $C_1$-$C_6$ alkylthio($C_1$-$C_6$)alkylthio group, or a $C_1$-$C_6$ alkylthio($C_1$-$C_6$)alkoxy group.

3. The compound according to claim 1, wherein $R_1$ is a methyl group, an ethyl group, an n-propyl group, an isopropyl group, a fluoromethyl group, a difluoromethyl group, a trifluoromethyl group or a tetrafluoroethyl group.

4. The compound according to claim 1, wherein $R_4$ is a methyl group, an ethyl group, an n-propyl group, an isopropyl group, a fluorine atom, a bromine atom, or a chlorine atom.

5. The compound according to claim 1, wherein $R_5$ is a methyl group, an ethyl group, an n-propyl group, or an isopropyl group.

6. The compound according to claim 1, wherein $R_1$ is a methyl group, $R_5$ is a hydrogen atom and X is an oxygen atom.

7. The compound according to claim 1, wherein $R_1$ is a methyl group, $R_2$ is an ethoxy group at the 4-position, $R_3$ is a hydrogen atom, $R_5$ is a hydrogen atom and X is an oxygen atom.

8. The compound according to claim 1, which is represented by the formula:

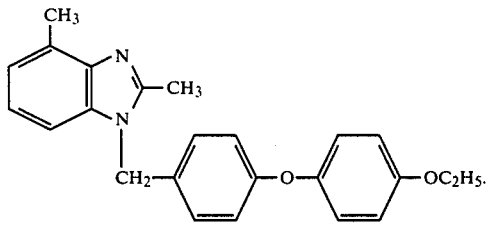

9. The compound according to claim 1, which is represented by the formula:

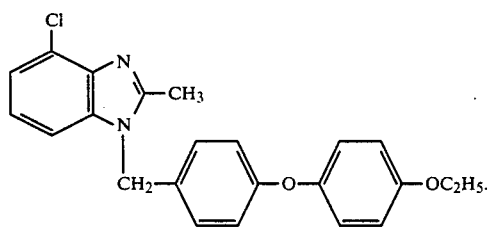

10. The compound according to claim 1, which is represented by the formula:

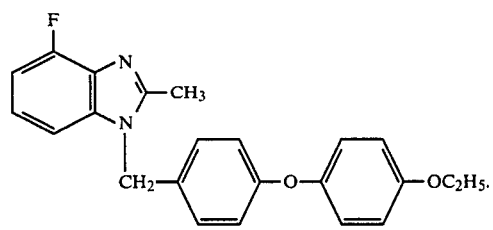

11. An insecticidal and/or acaricidal composition which comprises as an essential active ingredient an insecticidally and/or acaricidally effective amount of the compound according to claim 1 and an inert carrier or diluent.

12. A method for controlling or exterminating insects and/or acarids which comprises applying as the active ingredient an insecticidally and/or acaricidally effective amount of the compound according to claim 1 to the locus where insects and/or acarids propagate.

* * * * *